United States Patent [19]

Tolman

[11] Patent Number: 4,931,433
[45] Date of Patent: Jun. 5, 1990

[54] METHOD FOR TREATING CERTAIN NEOPLASTIC DISEASES

[75] Inventor: Richard L. Tolman, Warren, N.J.

[73] Assignee: Merck & Co., Inc., Rahway, N.J.

[21] Appl. No.: 45,256

[22] Filed: May 1, 1987

Related U.S. Application Data

[63] Continuation of Ser. No. 858,092, Apr. 29, 1986 abandoned, which is a continuation of Ser. No. 748,070, Jun. 24, 1985 abandoned.

[51] Int. Cl.$^5$ .......................................... H61K 31/635
[52] U.S. Cl. ................................................... 514/157
[58] Field of Search ........................................ 514/157

[56]  References Cited

PUBLICATIONS

Stock et al., Cancer Research, vol. 20, Jun. 1960, No. 5, Part 2, pp. 193-195 and 228.
Chemical Abstracts: 43: 33839-3384e (1949).

Primary Examiner—Jerome D. Goldberg
Attorney, Agent, or Firm—Hesna J. Pfeiffer; Charles M. Caruso

[57] ABSTRACT

Compounds of formula I are formulated with a pharmaceutical carrier for the treatment of neoplastic disease sensitive to treatment with the compounds in animals including humans.

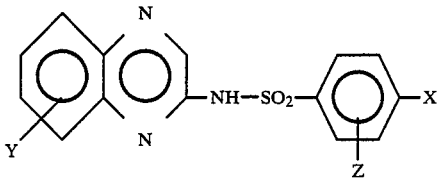

wherein:
Y is a substituent attached to any of the unsubstituted carbons on the quinoxaline ring selected from $NO_2$, $OCH_3$, H, chloro, $CH_3$, bromo, hydroxy;
X is selected from $NO_2$, $NH_2$, acylamide; and
Z is hydrogen or halo.

3 Claims, No Drawings

METHOD FOR TREATING CERTAIN NEOPLASTIC DISEASES

This is a continuation of application Ser. No. 858,092, filed 4/29/86, now abandoned, which is a continuation of application Ser. No. 748,070, filed 6/24/85, now abandoned.

BACKGROUND OF THE INVENTION

The present invention relates generally to sulfonamido derivatives of sulfanilamido quinoxaline of formula I and the use of such compounds in the treatment of neoplastic disease sensitive to treatment with the compound in animals including humans.

Pertinent to the background of this invention is the compound 2-(4-aminobenzenesulfonamido)-quinoxaline also known as sulfaquinoxalin which has been used as a coccidiostat in the prophylactic treatment of chickens and other fowl to prevent the onset of coccidiosis disease. Also pertinent to the present invention is an article published by F. J. Wolf et al., *Substituted Sulfaquinoxaline III Extension of the Glyoxalate Synthesis of 2-Aminoquinoxaline*, J. Am. Chem. Soc. 71, 6-10 (1947) which describes the synthesis of a number of similarly substituted sulfaquinoxaline and a general method of synthesis for such compounds by reaction of the substituted 2-aminoquinoxaline compound with a p-acetylaminobenzenesulfonyl chloride to produce the substituent of the 2-$N^4$-acetylsulfanilamide quinoxaline and hydrolyzing said acetyl compound by heating with 2.5N aqueous sodium hydroxide to produce the desired 2-sulfanilamido substituted quinoxaline.

DESCRIPTION OF THE INVENTION

In accordance with the present invention a compound of formula I hereinbelow:

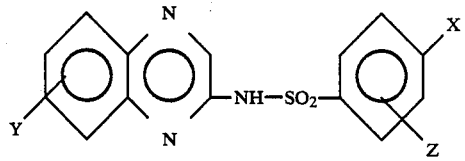

wherein:
X is a substituent selected from —$NO_2$, —$NH_2$,

NH—$(CH_2)_n$—COOH or $NHCH_2SO_3H$; wherein R is lower alkyl or phenyl and N=1 to 6;

Y is a substituent attached to any carbon in the quinoxaline ring selected from $NH_2$, $OCH_3$, halogen (including chloro, bromo and fluoro), —$CH_3$, OH; and Z is hydrogen or halogen;

is mixed with a non-toxic pharmaceutical carrier and divided into unit doses, each dose containing an effective neoplasm-inhibiting amount of the selected sulfanilamidoquinoxaline to produce a pharmaceutical composition effective in treating neoplastic disease sensitive to treatment and administering said composition to the animal host having a neoplastic disease sensitive to treatment.

Preparation of Active Compounds

The compounds active as agents against neoplastic disease sensitive to treatment with the compounds of formula I hereinabove are prepared in accordance with the procedure set forth in the article by F. J. Wolf et al., *Substituted Sulfaquinoxaline III Extension of the Glyoxalate Synthesis of 2-Aminoquinoxaline*, J. Am. Chem. Soc. 71, 6-10 (1947). The process described therein comprises treatment of an appropriately substituted 2-aminoquinoxaline with a p-nitro- or p-acetylaminobenzenesulfonyl chloride in dry pyridine and if desired to produce the corresponding 2-(4-nitrobenzenesulfonylamido)quinoxaline or the 2-$N^4$-acetylsulfanilamidoquinoxaline and if desired hydrolyzing the N-acetyl compounds to produce the corresponding 2-sulfanilamidoquinoxaline as illustrative herein below:

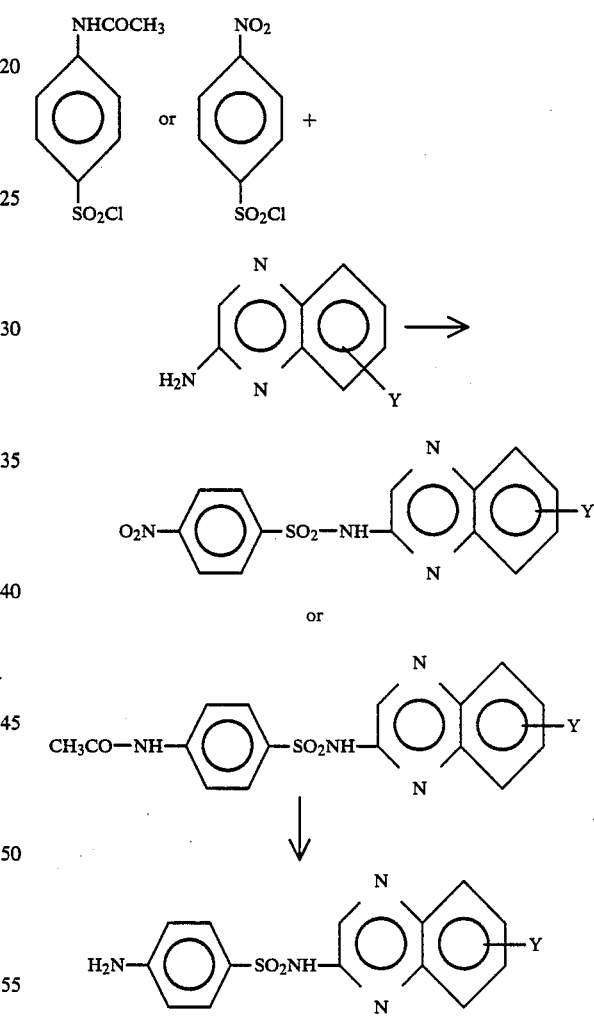

Compounds prepared in this manner are:

|  | MP |
| --- | --- |
| 2-(4-nitrobenzenesulfonylamido)-quinoxaline | |
| 2-sulfanilamido-quinoxaline | |
| 2-sulfanilamido-6 (or 7)-methyl quinoxaline a | 215–16° C. |
| 2-sulfanilamido-6 (or 7)-methyl quinoxaline b | 255–56° C. |
| 2-sulfanilamido-6 (or 7)-chloro quinoxaline a | 248–49° C. |
| 2-sulfanilamido-6 (or 7)-chloro quinoxaline b | 238–39° C. |
| 2-sulfanilamido-6 (or 7)-bromo quinoxaline a | 244–46° C. |
| 2-sulfanilamido-6 (or 7)-bromo quinoxaline b | 239–40° C. |
| 2-sulfanilamido-6 (or 7)-nitro quinoxaline a | 220–21° C. |

| | MP |
|---|---|
| 2-sulfanilamido-6 (or 7)-nitro quinoxaline b | 224–26° C. |
| 2-sulfanilamido-6 (or 7)-amino quinoxaline a | 275–76° C. |
| 2-sulfanilamido-6 (or 7)-methoxy quinoxaline a | 239–40° C. |
| 2-sulfanilamido-6 (or 7)-methoxy quinoxaline b | 235–37° C. |
| 2-sulfanilamido-6 (or 7)-carboxy quinoxaline b | 223–20 C. |
| 2-sulfanilamido-5 (or 8)-methyl quinoxaline a | 205–06° C. |
| 2-sulfanilamido-5 (or 8)-methyl quinoxaline b | 192–94° C. |
| 2-sulfanilamido-5 (or 8)-methoxy quinoxaline b | 105° C. |
| *2-sulfanilamido-5-chloroquinoxaline b | 213–15° C. |
| 2-sulfanilamido-5-methyl-6-chloro-8-isopropyl-quinoxaline b and isomer | 92–115° C. |

*The structure of this compound was determined absolutely by X-ray spectroscopy.

In the preceeding list of compounds a refers to the lower melting isomer and b to the higher melting isomer.

The therapeutic methods of the present invention comprise the administration of effective amounts of one or more of the compounds of Formula I as an active ingredient together with desired pharmaceutically acceptable diluents, adjuvants and carriers to an animal suffering from a neoplastic disease sensitive to treatment with the compounds. Unit dosage forms of compound of from 0.1 to 500 mg are administered according to the methods of the invention. Such unit dosage forms may be given to provide a daily dosage of from 10 to 500 mg/kg of body weight of the animal to be treated. Parenteral administration and especially intraperitoneal administration is the preferred route for practice of the invention methods.

The following examples are for illustrative purposes only and are not considered limiting the invention.

EXAMPLE 1

In Vitro Activity of 2-Sulfanilamido-5-chloroquinoxaline

Tests carried out in accordance with the procedures described in Cancer Research 45, 2145–53, May 1985, *Application of a Human Tumor Colony-forming Assay to New Drug Screening* - Shoemaker et al.

| | Colony Forming Assay Reponse Rates For 9 Tumor Type | | |
|---|---|---|---|
| | Dose meq/ml | | |
| Tumor Type | 10 | 1 | 0.1 |
| Breast | 2/6 (33.3%) | ¼ (25%) | 0/4 (0%) |
| Colorectal | 2/10 (20%) | 2/10 (0%) | 0/10 (0%) |
| Kidney | 3/10 (30%) | ¼ (11.1%) | 0/0 (0%) |
| Lung | 5/11 (45%) | ⅜ (38%) | ⅛ (13%) |
| Melanoma | 4/13 (30.8%) | 2.8 (25%) | 0/8 (0%) |
| Ovary | 6/16 (37.5%) | 0/9 (0%) | 1/7 (14.3%) |
| Sarcoma | 1/1 (100%) | NT | NT |
| Skin | 0/1 (0%) | NT | NT |
| Uterine | ½ (50%) | NT | NT |

Total for all tumors at 10 meq/ml - 24/70 (34.3%)
Total for all tumors at 1 meq/ml - 7/48 (14.6%)
Total for all tumors at 0.1 meq/ml - 2/47 (4.3%)
Response = = 70% cell kill at = 10 meq/ml
NT - Test faulted and experiment not included

EXAMPLE 2

In Vivo Activity of 2-Sulfanilamido-5-chloroquinoxaline

The test for antitumor activity in vivo using a new human tumor xenograft model, the LOX amelanotic melanoma in mice showed a significant increase in the life span of mice when treated with the title compound in doses of 449, 300 and 200 mg/kg/day.

What is claimed is:

1. A method of treating neoplastic disease sensitive to treatment with the compound below in animals including humans which comprises administering an effective amount of a compound of the formula:

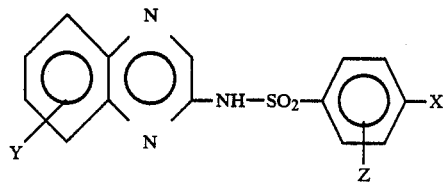

wherein:
Y is chloro attached to any of the unsubstituted carbon atoms on the quinoxaline ring;
X is $NH_2$; and
Z is hydrogen;
to the affected animal.

2. A method of treating neoplastic disease in animals which comprises administering an effective amount of 2-sulfanilamido-5-chloroquinoxaline to an animal affected by said neoplastic disease.

3. A method according to claim 2 wherein the amount of the 2-sulfanilamido-5-chloro-quinoxaline administered comprises a daily dose of from about 10 to 500 mg per kg of the body weight.

* * * * *